United States Patent [19]

Audhya et al.

[11] Patent Number: 4,584,284

[45] Date of Patent: Apr. 22, 1986

[54] BURSOPOIETIN

[75] Inventors: Tapan Audhya; Daniel J. Kroon, both of Bridgewater; George Heavner, Flemington; Gideon Goldstein, Short Hills, all of N.J.

[73] Assignee: Ortho Pharmaceutical Corporation, Raritan, N.J.

[21] Appl. No.: 681,971

[22] Filed: Jan. 31, 1985

[51] Int. Cl.$^4$ ...................... A61K 37/24; C07K 5/08; C08F 283/00
[52] U.S. Cl. .............................. 514/18; 260/112.5 R; 525/54.11
[58] Field of Search ................... 514/18; 260/112.5 R; 525/54.11

[56] References Cited

PUBLICATIONS

Brand, et al., Science, vol. 193, pp. 319–321 (Jul. 23, 1976).
Brand, et al., Nature, vol. 269, pp. 597–598 (Oct. 13, 1977).
Goldstein, et al., Cold Spring Harbor Symposia on Quantitative Biology, vol. XLI, pp. 5–8 (1977).
Goldstein, in "Molecular Control of Proliferation and Differentiation, pp. 197–202, Academic Press (1977).

Primary Examiner—Delbert R. Phillips
Attorney, Agent, or Firm—Geoffrey G. Dellenbaugh

[57] ABSTRACT

A synthetic peptide which possesses the ability to specifically induce the differentiation of precursor B cells into mature B-cells capable of producing antibody.

6 Claims, 1 Drawing Figure

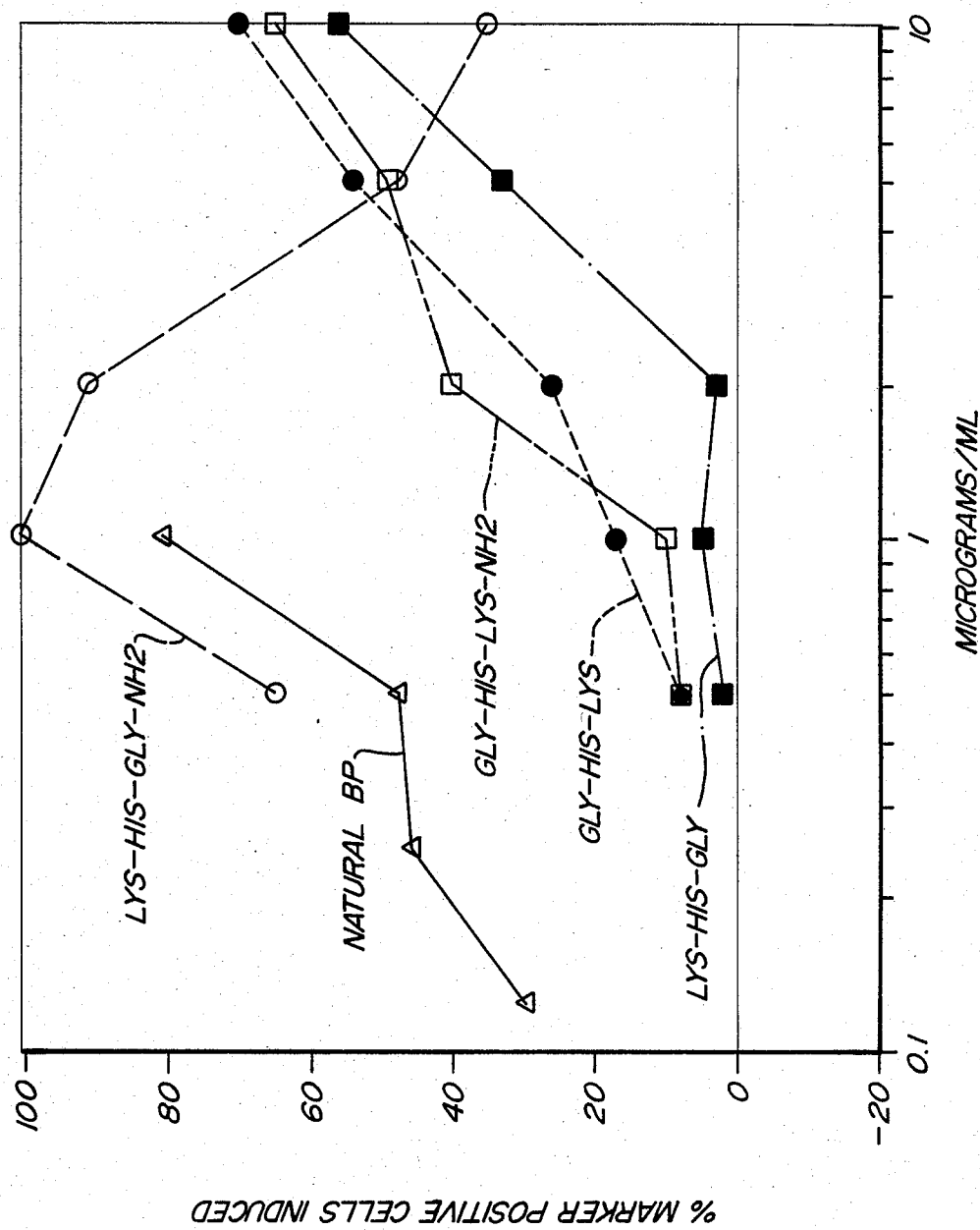

BURSOPOIETIN

BACKGROUND OF THE INVENTION

This invention relates generally to new peptides and particularly to a new synthetic peptide which induces selective B-cell differentiation.

Two main classes of lymphocytes occur in the immune system of vertebrate animals: (1) T-lymphocytes or T-cells, which differentiate in the thymus, and (2) B-lymphocytes or B-cells, which differentiate in the Bursa of Fabricius of birds and presumably in some homologous organ in vertebrates, which have no bursa. The immediate precursors of T-cells and B-cells are found in the bone marrow and are induced by specific hormones or "inducers" to differentiate into the mature cells. In the case of T-cells, the inducer is the polypeptide thymopoietin, which has been extensively studied. See, for example, U.S. Pat. Nos. 4,002,740, 4,077,949, and 4,190,646, of which one of the inventors herein is either the inventor or a co-inventor.

To provide a general understanding of the importance of the differentiating biological characteristics of the peptide of this invention, it should be noted that the function of the thymus in relation to immunity may be broadly stated as the production of thymus-derived lymphocytes (called T-cells). T-cells form a large proportion of the pool of recirculating small lymphocytes. They have immunological specificity and are directly involved in cell-mediated immune responses (such as homograft responses) as effector cells. T-cells, however, do not secrete antibodies, this function being performed by a separate class of lymphocytes termed B-cells. B-cells are derived from precursor B-cells in the bone marrow independent of thymic influence. In birds, they are differentiated in an organ analogous to the thymus which is called the Bursa of Fabricius. In mammals, no equivalent organ has been discovered, and it is thought that B-cells may differentiate within the bone marrow itself. The physiological substance dictating this differentiation remained completely unknown until the present invention.

In early studies by one of the present inventors and others, the existence of a specific B-cell differentiating inducer was demonstrated in extracts of the Bursa of Fabricius from chickens. The active material in this extract was not characterized, although the authors of one of the early articles stated that they "infer that it is a small polypeptide." This early work is reported in the following articles, which are incorporated herein by reference: Brand, et. al., Science, Volume 193, pgs. 319-321 (July 23, 1976); Brand, et. al., Nature, Vol. 269, pgs. 597-598 (October 13, 1977); Goldstein, et. al., Cold Spring Harbor Symposia on Quantitative Biology, Vol. XLI, pgs. 5-8 (1977); and Goldstein, in "Molecular Control of Proliferation and Differentiation", pgs. 197-202, Academic Press (1977).

The discovery of a specific B-cell differentiating factor would be of considerable value in understanding the immune function and in diagnosing and treating various immune disorders in humans and animals. For example, a rare but potentially fatal disease called hypogammaglobulinemia manifests itself as an inability or severe deficiency of an individual to produce antibodies. Such an individual is susceptible to unchecked infection and has a relatively short life expectancy. While it is believed that this disease may have several causes, at least one cause is the absence of functional B-cells. If the absence of functional tional B-cells is due to an underproduction of the B-cell differentiating hormone, administration of this hormone would restore the patient to normal.

The present invention provides a synthetic 3-amino acid peptide having the specific B-cell differentiating function of bursopoietin.

SUMMARY OF THE INVENTION

It is accordingly one object of this invention to provide a new synthetic peptide which is biologically important.

A further object of the invention is to provide a new synthetic peptide which has the ability to specifically induce differentiation of precursor bone marrow cells to B-cells and thereby is highly useful in the immune system of humans and animals.

A further object of the invention is to provide novel intermediates for preparation of the biologically-important peptide, methods for synthesizing the peptide of the invention, and compositions and methods for diagnosis and therapy.

Other objects and advantages of this invention will become apparent as the description proceeds.

In satisfaction of the foregoing objects and advantages, there is provided by this invention the novel peptide having the following formula:

H-LYS-HIS-GLY-NH$_2$ and biologically-active pharmaceutically-acceptable acid-addition salts thereof.

The invention also provides novel peptide-resin intermediates for preparation of the peptide of the invention, said intermediates having the following formula:

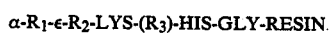

$\alpha$-R$_1$-$\epsilon$-R$_2$-LYS-(R$_3$)-HIS-GLY-RESIN wherein R$_1$ and R$_2$ represent suitable amino-protecting groups on the appropriate locations of the indicated amino acids, R$_3$ is an appropriate imidazole-protecting group, and the resin is a suitable solid phase polymer which acts as a support for the reaction. Those of ordinary skill in the peptide synthesis art could select the appropriate amino-protecting groups, imidazole-protecting qroup, and resin, disclosed for example, in the Bodanszky reference noted below.

Also provided by the present invention are methods of selectively inducing the differentiation of B-cells of humans and animals, both in vivo and in vitro, as well as selective B-cell differentiation inducing compositions. Further provided are methods for treating conditions or diseases involving insufficient B-cell differentiation due to a deficiency or lack of B-cell differentiating factor which comprises administration of the peptide of the invention.

BRIEF DESCRIPTION OF THE FIGURE

FIG. 1 is a graphical depiction of the results of testing the claimed peptide and other related peptides.

DETAILED DESCRIPTION OF THE INVENTION

As indicated above, this invention in concerned with a new synthetic peptide, intermediates for preparing this peptide, methods of using the peptide and compositions containing the peptide.

The preferred embodiment of the present invention is the synthetic peptide of formula:

H-LYS-HIS-GLY-NH$_2$ and the pharmaceutically-acceptable acid-addition salts thereof.

As acids which are able to form salts with the tripeptide of the invention, there may be mentioned inorganic acids such as hydrochloric acid, hydrobromic acid, perchloric acid, nitric acid, thiocyanic acid, sulfuric acid, carbonic acid, phosphoric acid, and the like, and organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid, sulfanylic acid, and the like.

In the above structure, the amino acid components of the tripeptide are identified by abbreviations for convenience. Moreover, other materials described in the specification are also identified by abbreviations. These abbreviations are as follows:

| Chemical | Abbreviation |
| --- | --- |
| Glycine | GLY |
| L-histidine | HIS |
| L-lysine | LYS |
| t-Butyloxycarbonyl | BOC |
| Trifluoroacetic acid | TFA |
| Hydrogen fluoride | HF |
| Benzyloxycarbonyl | Z |
| Acetic acid | HOAc |
| Propanol | PrOH |
| Pyridine | Pyr |

The tripeptide of this invention has been found to exhibit the characteristics of naturally-occurring bursopoietin. It is particularly characterized by their ability to induce the selective differentiation of Lyb-2+ B-cells (but not Thy-1+ T-cells) in concentrations of about 1 μg/ml in the assay described in Audhya, et. al., Proc. Natl. Acad. Sci. USA, 81, 2847-49 (1984). Lyb-2 is a differentiation alloantigen present on B-cells but not on T-cells, while Thy-1 is a differentiation alloantigen present on T-cells but not on B-cells.

Although several substances (including the material designated as "ubiquitin" and referred to in certain of the above-referenced articles) are able to nonselectively induce the differentiation of both T-cells and B-cells, the subject material is the first material of known structure able to selectively induce the differentiation of B-cells.

Because of this characteristic of the peptide of this invention, it are useful to induce the differentiation of precursor bone marrow cells into mature B-cells. Thus, the subject invention includes a method of inducing the selective differentiation of precursor B-cells to mature B-cells either in vitro or in vivo which comprises contacting said precursor B-cells with an effective differentiation-inducing amount of the peptide of the invention. Therefore, the subject peptide has utility not only in research but also in the treatment of humans and animals for diseases relating to a deficiency or absence of mature B-cells. Since this peptide has the capability of inducing the differentiation of lymphopoietic stem cells originating in the hemopoietic tissues to mature B-cells which are capable of involvement in the immune response of the body, it has utility wherever there is a defect in humoral immunity resulting from a deficiency or absence of the hormone for inducing B-cell differentiation.

A typical condition which would be amenable to treatment with the subject peptide would be so-called X-linked infantile hypogammaglobulinemia. This disease, first reported by Bruton in 1952, was the first clinical description of an immunodeficiency disorder. As its name implies, it occurs almost exclusively in male children and manifests itself following the natural decay of transplacentally-acquired maternal immunoglobulin at about 5-6 months of age. The disorder is easily diagnosed by standard laboratory tests which demonstrate a marked deficiency or complete absence of all five immunoglobulin classes. It appears that sufferers from this condition have precursor B-cells in their marrow and peripheral blood, but these precursor B-cells do not mature to antibody-secreting B-cells.

Patients having this condition suffer from chronic or recurring bacterial infections.

Although this condition is now commonly treated by administration of gammaglobulin, such treatment should not be considered a cure for the disease. Moreover, although gammaglobulin replacement therapy may appear to be adequate in some instances, many patients develop chronic lung disease or may suffer from irreversible damage from severe infection early in infancy.

Other immunodeficiencies involving absent or lowered immunoglobulin production may also be amenable to treatment with the subject peptide, depending on the location of the immunological defect giving rise to this problem. If the defect is in the maturation of the pre-B-cell into the mature antibody-secreting B-cell, then the subject peptide would be of use. If the defect is at some other point in the immunologic structure, (for example, a deficiency or defect in the bone marrow stem cells), then administration of the subject peptide would not be expected to be effective to remedy the defect. It is well within the scope of the clinician of average skill in the art of treating immunodeficiencies to diagnose the point of defect for such diseases and to select the appropriate treatment.

For a further discussion of these immunodeficiencies and their current treatments the reader is directed to "Basic and Clinical Immunology", Stites, Stobo, Fudenberg, and Wells, Editors, 4th Edition, 1982, Lange Medical Publications, Los Altos, California, with particular reference to Chapter 25.

The invention includes a method of treating B-cell deficiency resulting from a defect or deficiency in the differentiation of precursor stem cells into B-cells in a patient suffering from same which comprises administering to said patient an effective precursor stem cell differentiating amount of the peptide of the subject invention. Since the peptide of the invention is maximally active at about 1 μg/ml, it would be active at about 1 mg/kg of body weight when administered parenterally. For the treatment of X-linked hypogammaglobulinemia, the peptide may be administered parenterally in a range of from about 1 to about 10 mg/kg of body weight. One of ordinary skill in the immunodeficiency treatment art would readily be able to extrapolate from the results herein and select the appropriate dosage of the subject peptides without undue experimentation.

The subject peptide may conveniently be administered in pharmaceutical compositions containing a carrier, and said compositions are a further aspect of the subject invention. The carrier may be any of the well-known carriers for this purpose. Since it is contemplated that these materials would be principally administered by injection, the typical carrier would be normal saline solution. Those of skill in the parenteral formulation art would readily recognize how to prepare such a composition.

The tripeptide of the invention was prepared using the solid-phase synthetic method first described by Merrifield in J.A.C.S., Vol. 85, pgs. 2149-2154 (1963). This technique is well understood and is a common method for preparation of peptides. Useful techniques for solid-phase peptide synthesis are described in several books such as the text "Peptide Synthesis" by Bodanszky, et al., second edition, John Wiley and Sons, 1976. This method of synthesis involves the stepwise addition of protected amino acids to a growing peptide chain which was bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond, followed by the addition of the succeeding protected amino acids, one at a time, in a stepwise manner until the desired sequence is assembled. Finally, the protected peptide is removed from the solid resin support and the protecting groups are cleaved off.

The amino acids may be attached to any suitable polymer. The polymer must be insoluble in the solvents used, must have a stable physical form permitting ready filtration, and must contain a functional group to which the first protected amino acid can be firmly linked by a covalent bond. Various polymers are suitable for this purpose, such as cellulose, polyvinyl alcohol, polymethylmethacrylate, and polystyrene. For preparation of the subject peptide amide, a para-methylbenzhydrylamine copolymer of styrene and divinylbenzene was used, while for preparation of the unamidated peptides, a chloromethylated copolymer of styrene and divinylbenzene was used.

The general procedure of preparation involved initially amidating the glycine (protected on its amino group) to the resin (in solvents). After the coupled glycine resin was filtered, washed, and dried, the protecting group on the amino group of the protected glycine was removed. This protecting group is conveniently t-butyloxycarbonyl, abbreviated BOC. The removal of this protecting group must take place, of course, without breaking the bond between the glycine and the resin. To the resulting coupled amino acid-resin was then coupled L-histidine protected on its amino and imidazole groups. The coupling took place by the formation of an amide bond between the free amino group of the glycine amino acid and the free carboxyl group of the L-histidine amino acid.

Next, the protective group was removed from the amino group of L-histidine without disturbing the bonds between the amino acids or between the glycine and the resin or the protecting group on the imidazole group of histidine and a L-lysine amino acid (protected on both amino groups) is coupled. Finally, the protected peptide was cleaved from the resin and the protecting qroups were removed, yielding the desired peptide.

In the following preparative examples, the common abbreviations for protecting groups and solvents are employed. Reference is made to the above-mentioned texts, articles, and patents, where these abbreviations may be found.

If it is desired to prepare an acid-addition salt of the subject peptide, this can be accomplished by treating the free peptide with the appropriate amount of acid.

The following examples are presented to illustrate the subject invention. The invention is not to be considered limited by these examples, but only by the appended claims. In the examples and throughout the specification, parts are by weight unless otherwise indicated.

EXAMPLE I

L-Lysyl-L-Histidyl-Glycine

The peptide was synthesized by the solid phase method. The synthesis was begun with 3.00 g of BOC-Gly-resin ester, 0.69 meg per gram. The resin was deprotected with 50 percent TFA/$CH_2Cl_2$ for 30 minutes, neutralized twice with 7 percent DIEA/$CH_2Cl_2$, and coupled with 3 equivalents of amino acid derivative and dicyclohexylcarbodiimide. BOC-His(tosyl) and BOC-Lys(Z) were coupled in sequence. The BOC group was removed with TFA/$CH_2Cl_2$, then the resin was washed and dried. The peptide resin weighed 4.06 g. The resin was treated with 40 ml of distilled HF and 4 ml anisole for 1 hour at 0°. After removal of the HF with vacuum, the resin was washed with ethyl acetate and the peptide extracted with 10 percent acetic acid. The filtered extract was lyophilized to yield the crude peptide weighing 530 mg.

The peptide was purified by chromatography on CM-Sephadex eluted with a gradient of 0.2N pH 6.0 to 0.50M pH 7 ammonium acetate. Fractions containing the purified peptide were lyophilized yielding a hygroscopic glass weight approximately 800 mg.

TLC, silica gel 60: $R_f$ 0.19, 4:1 TFE/$NH_4OH$; $R_f$ 0.29 4:2:3:1 n-BuOH/HOAc/$H_2O$/pyr; $R_f$ 0.60, 1:1 n-PrOH/$NH_4OH$.

Amino acid analysis: Gly, 0.96; His, 1.02; Lys, 1.02; 39 percent peptide.

EXAMPLE II

L-Lysyl-L-Histidyl-Glycineamide

The peptide was synthesized by the solid phase method on a p-methylbenzhydrylamine PS-DVB resin. The resin was neutralized with 5 percent DIEA/$CH_2Cl_2$, then coupled with 3 equivalents of BOC-Gly and dicyclohexylcarbodiimide for 3 hours. The resin was washed, then deprotected with 50 percent TFA/$CH_2Cl_2$ for 30 minutes and neutralized and coupled as before with BOC-His(tosyl). The cycle was repeated with BOC-Lys(Z). The weight of the washed and dried resin was 1.93 g. The material was reacted with 25 ml distilled HF containing 2 ml anisole at 0° for one hour. The HF was removed with vacuum and the residue washed with ethyl acetate and ether. The peptide was extracted into 5 percent acetic acid. The extract was lyophilized, yielding 110 mg of hygroscopic glass.

The peptide was purified by chromatography on SP-Sephadex eluted with 0.50M unbuffered ammonium acetate. The fractions containing the major peak of the chromatograph were lyophilized to give the product as a hygroscopic glass.

TLC, silica gel 60: $R_f$ 0.11, 4:1 TFE/$NH_4OH$; $R_f$ 0.25 4:2:3:1 n-BuOH/HOAc/$H_2O$/pyr; $R_f$ 0.49 1:1 n-

PrOH/NH₄OH. Amino acid analysis: Gly, 1.00; His, 0.99; Lys, 1.00: 62 percent peptide.

EXAMPLE III

Following the procedures of Examples I and II, there were prepared glycyl-L-histidyl-L-lysine and glycyl-L-histidyl-L-lysineamide.

EXAMPLE IV

To determine the activity and immunological characteristics of the subject peptide, the related peptides prepared in the above Examples, and natural bursopoietin, an induction assay was carried out substantially as described in Audhya, et al., Proc. Natl. Acad. Sci. USA, 81, 2847 (1984).

In brief, prothymocytes (Thy-1⁻) and pro-Lyb-2 cells were coenriched from B6-Lyb-2.1 congenic mouse spleen by bovine serum albumin density gradient centrifugation (Path-O-Cyte 5, lot 35, 1 ml of 35/29/26/23/18/12%). The 26/23 and 23/18 interface layers were combined, and Thy-1⁺ and Lyb-2⁺ cells were removed by reaction with monoclonal Thy-1.2 and Lyb-2.1 antibodies prepared according to Scheid, et al., Immunogenetics, 9, 423–433 (1979), and adherence to plates coated with affinity-purified rabbit anti-mouse F(ab)₂. The washed nonadherent cells were used for both assays. This starting population contained 30–40% prothymocytes and 30–40% pro-Lyb-2 cells (known to represent separate committed precursor populations) as described in Scheid, et al., J. Exp. Med., 147, 1727–1743 (1978).

Cells (5×10⁶ cells per 0.5 ml of RPMI 1640 medium) were incubated in 5-ml plastic tubes with equal volumes of test compound in serial dilution in RPMI 1640 medium in a humidified 5% CO₂ atmosphere for 3 hr. The cells were then assayed separately for Thy-1 and Lyb-2 expression with monoclonal antibodies in optimal concentration by the staphylococcal protein A-sheep erythrocyte method described in the first-mentioned Scheid, et al., reference (controls without inducer registered <5% induced cells).

The results of this determination are presented in FIG. 1. As can be seen from these results, the subject peptide possessed the activity of the natural isolate, while the related peptides of Examples I and III were virtually inactive at the same concentration.

The invention has been described herein with reference to certain preferred embodiments. However, since obvious variations will appear to those skilled in the art, the invention is not to be considered as limited thereto.

What is claimed is:

1. A peptide of formula H-LYS-HIS-GLY-NH₂ and the pharmaceutically acceptable acid-addition salts thereof.

2. A method of inducing the selective differentiation of precursor B cells cells into mature B cells which comprises contacting said precursor B cells with an effective differentiation-inducing amount of the peptide of claim 1.

3. A method of treating B cell deficiency resulting from a defect or deficiency in the differentiation of precursor B cells into mature B cells in a patient suffering from same which comprises administering to said patient an effective precursor B cell differentiating amount of the peptide of claim 1.

4. A therapeutic composition comprising an effective precursor B cell differentiating amount of a peptide of claim 1 in admixture with a pharmaceutically acceptable carrier.

5. The composition of claim 4 which is adapted for parenteral administration.

6. A peptide-resin intermediate of formula α-R₁-ε-R₂-LYS-(R₃)-HIS-GLY-RESIN wherein R₁ and R₂ are each independently selected from appropriate amino-protecting groups, R₃ is an appropriate imidazole-protecting groups, and RESIN is an appropriate solid phase polymer.

* * * * *

UNITED STATES PATENT AND TRADEMARK OFFICE
CERTIFICATE OF CORRECTION

PATENT NO. : 4,584,284
DATED : April 22, 1986
INVENTOR(S) : Audhya et al.

It is certified that error appears in the above-identified patent and that said Letters Patent is hereby corrected as shown below:

Claim 6, line 37 delete "groups," and insert -- group, --

Signed and Sealed this

Twelfth Day of August 1986

[SEAL]

Attest:

DONALD J. QUIGG

Attesting Officer

Commissioner of Patents and Trademarks